United States Patent
Murakita

(10) Patent No.: US 11,523,729 B2
(45) Date of Patent: Dec. 13, 2022

(54) SURGICAL CONTROLLING DEVICE, CONTROL METHOD, AND SURGICAL SYSTEM

(71) Applicant: SONY CORPORATION, Tokyo (JP)

(72) Inventor: Masashi Murakita, Chiba (JP)

(73) Assignee: SONY CORPORATION, Tokyo (JP)

( * ) Notice: Subject to any disclaimer, the term of this patent is extended or adjusted under 35 U.S.C. 154(b) by 361 days.

(21) Appl. No.: 16/494,006

(22) PCT Filed: Feb. 21, 2018

(86) PCT No.: PCT/JP2018/006225
§ 371 (c)(1),
(2) Date: Sep. 13, 2019

(87) PCT Pub. No.: WO2018/173605
PCT Pub. Date: Sep. 27, 2018

(65) Prior Publication Data
US 2021/0121046 A1    Apr. 29, 2021

(30) Foreign Application Priority Data
Mar. 22, 2017 (JP) .............................. JP2017-056091

(51) Int. Cl.
*A61B 1/00* (2006.01)
*A61B 1/045* (2006.01)
(Continued)

(52) U.S. Cl.
CPC ...... *A61B 1/00009* (2013.01); *A61B 1/00006* (2013.01); *A61B 1/045* (2013.01); *A61B 1/06* (2013.01); *A61B 1/313* (2013.01)

(58) Field of Classification Search
CPC . A61B 1/00009; A61B 1/00006; A61B 1/045; A61B 1/06; A61B 1/313
See application file for complete search history.

(56) References Cited

U.S. PATENT DOCUMENTS 4,349,255 A * 9/1982 Takayama .............. A61B 1/045
   396/17
5,523,786 A * 6/1996 Parulski ............... H04N 5/2353
   348/269
(Continued)

FOREIGN PATENT DOCUMENTS

CN       107529975 A    1/2018
JP       2013-042998 A  3/2013
(Continued)

OTHER PUBLICATIONS

International Search Report and Written Opinion of PCT Application No. PCT/JP2018/006225, dated May 22, 2018, 07 pages of ISRWO.

*Primary Examiner* — Timothy J Neal
*Assistant Examiner* — William B Chou
(74) *Attorney, Agent, or Firm* — Chip Law Group

(57) ABSTRACT

There is provided a surgical controlling device including an exposure controlling section that performs exposure control based on a luminance detection value detected from a biological image, in which the exposure controlling section corrects, on the basis of information regarding an identified surgical optical device, the luminance detection value so as to correct luminance unevenness arising from the surgical optical device. Further, there is provided a control method including performing, by a processor, exposure control based on a luminance detection value detected from a biological image, in which the performing the exposure control further includes correcting the luminance detection value so as to correct, based on information regarding an identified surgical optical device, luminance unevenness arising from the surgical optical device.

20 Claims, 9 Drawing Sheets

(51) Int. Cl.
*A61B 1/06* (2006.01)
*A61B 1/313* (2006.01)

(56) References Cited

U.S. PATENT DOCUMENTS

| | | | | |
|---|---|---|---|---|
| 6,441,845 | B1* | 8/2002 | Matsumoto | H04N 5/2352 348/65 |
| 6,707,485 | B1* | 3/2004 | Higuchi | H04N 5/2354 348/362 |
| 2011/0009702 | A1* | 1/2011 | Morishita | A61B 1/00096 600/178 |
| 2011/0273548 | A1* | 11/2011 | Uchiyama | A61B 1/0655 348/E7.085 |
| 2012/0113307 | A1* | 5/2012 | Watanabe | G06V 20/40 348/333.01 |
| 2013/0184530 | A1* | 7/2013 | On | A61B 1/06 600/168 |
| 2013/0335583 | A1* | 12/2013 | Murakita | H04N 5/2256 348/207.1 |
| 2014/0118517 | A1* | 5/2014 | Fueki | A61B 1/00006 348/65 |
| 2014/0184769 | A1* | 7/2014 | Ishihara | G06T 5/50 348/68 |
| 2014/0204187 | A1* | 7/2014 | Sasaki | G06T 7/33 348/65 |
| 2017/0196443 | A1* | 7/2017 | Murakita | H04N 5/243 |
| 2017/0230634 | A1* | 8/2017 | Takenouchi | G02B 23/26 |
| 2017/0366724 | A1* | 12/2017 | Murakita | A61B 1/045 |
| 2018/0139370 | A1* | 5/2018 | Ichiki | A61B 1/045 |

FOREIGN PATENT DOCUMENTS

| | | |
|---|---|---|
| JP | 2013-078591 A | 5/2013 |
| WO | 2016/185763 A1 | 11/2016 |

\* cited by examiner

SURGICAL CONTROLLING DEVICE, CONTROL METHOD, AND SURGICAL SYSTEM

CROSS REFERENCE TO RELATED APPLICATIONS

This application is a U.S. National Phase of International Patent Application No. PCT/JP2018/006225 filed on Feb. 21, 2018, which claims priority benefit of Japanese Patent Application No. JP 2017-056091 filed in the Japan Patent Office on Mar. 22, 2017. Each of the above-referenced applications is hereby incorporated herein by reference in its entirety.

TECHNICAL FIELD

The present disclosure relates to a surgical controlling device, a control method, a surgical system, and a program.

BACKGROUND ART

In recent years, for example, in the medical field or the like, a scene in which a biological image is captured and a technique based on the biological image is performed has been increased. Further, various devices relating to capturing of such a biological image described above have been developed. For example, PTL 1 discloses a technology for performing exposure control relating to capturing of a biological image.

CITATION LIST

Patent Literature

[PTL 1]
Japanese Patent Laid-Open No. 2013-42998

SUMMARY

Technical Problem

However, the technology disclosed in PTL 1 implements exposure control on the basis of acquired angle-of-view information of an optical system. Meanwhile, luminance unevenness of a biological image to be captured may arise from various factors. Therefore, it is hard to say that the technology disclosed in PTL 1 can achieve exposure control that sufficiently takes luminance unevenness arising from a characteristic of an optical system into consideration.

Therefore, the present disclosure proposes a surgical controlling device, a control method, a surgical system, and a program that are novel and improved in that they can implement exposure control with high accuracy that does not rely upon a characteristic of an optical system.

Solution to Problem

According to the present disclosure, there is provided a surgical controlling device including: an exposure controlling section configured to perform exposure control based on a luminance detection value detected from a biological image, in which the exposure controlling section corrects, on the basis of information regarding an identified surgical optical device, the luminance detection value so as to correct luminance unevenness arising from the surgical optical device.

Further, according to the present disclosure, there is provided a control method including performing, by a processor, exposure control based on a luminance detection value detected from a biological image, in which the performing the exposure control further includes correcting the luminance detection value so as to correct, on the basis of information regarding an identified surgical optical device, luminance unevenness arising from the surgical optical device.

Further, according to the present disclosure, there is provided a surgical system including a surgical optical device used to capture a biological image; and a surgical controlling device configured to perform exposure control based on a luminance detection value detected from the biological image, in which the surgical controlling device corrects, on the basis of information regarding the identified surgical optical device, the luminance detection value so as to correct luminance unevenness arising from the surgical optical device.

Further, according to the present disclosure, there is provided a program for causing a computer to function as a surgical controlling device including an exposure controlling section that performs exposure control based on a luminance detection value detected from a biological image, in which the exposure controlling section corrects, on the basis of information regarding an identified surgical optical device, the luminance detection value so as to correct luminance unevenness arising from the surgical optical device.

Advantageous Effect of Invention

As described above, according to the present disclosure, it is possible to implement exposure control that does not rely upon a characteristic of an optical system with high accuracy.

It is to be noted that the advantageous effect described above is not necessarily restrictive, and any advantageous effect indicated in the present specification or other advantageous effects that can be recognized from the present specification may be applicable together with the advantageous effect described above or in place of the advantageous effect described above.

DESCRIPTION OF EMBODIMENT

Figure 1:
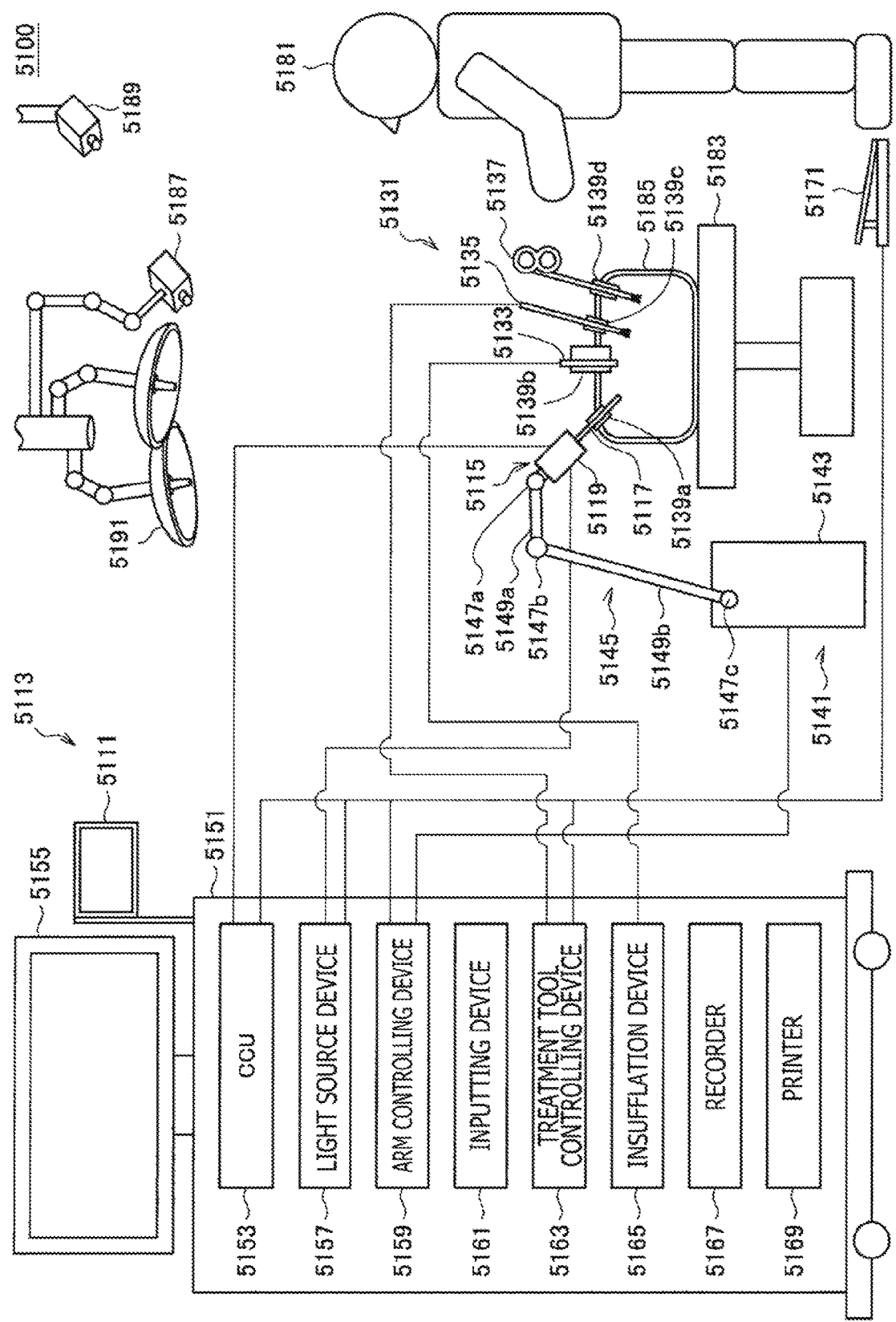
FIG. 1 is a view depicting an example of a manner of surgical operation to which an operating room system that uses the technical idea according to the present disclosure is applied.

In the following, a preferred embodiment of the present disclosure is described in detail with reference to the accompanying drawings. It is to be noted that, in the present specification and the drawings, components having substantially same functional configurations are denoted by same reference characters and overlapping description of them is omitted.

It is to be noted that the description is given in the following order.
1. Background
2. Example of Application
3. Embodiment
3.1. Example of System Configuration and Example of Functional Configuration
3.2. Details of Correction of Luminance Detection Value
3.3. Details of Identification of Optical Device
3.4. Flow of Operation of Control Device
4. Example of Hardware Configuration
5. Summary

1. Background

First, the background to the conceptualization of the present technical idea is described. As described hereinabove, in recent years, a scene in which a technique based on a captured biological image is performed has been increased. As such a technique as described above, for example, endoscopic surgery using an endoscope is available. According to the endoscopic surgery, by capturing a biological image relating to an observation object (patient) by the endoscope inserted in the observation object, the surgeon can perform inspection or technique while observing the biological image.

A technology is known by which, on this occasion, for example, a luminance value histogram is generated from luminance detection values relating to captured biological images and exposure control is performed on the basis of a degree of separation of the peak medians in the luminance value histogram.

Meanwhile, in endoscopic surgery, luminance unevenness often occurs in a captured biological image due to a characteristic of an optical device used for imaging. Here, the luminance unevenness described above includes, for example, shading arising from the optical device. The shading refers to a phenomenon that peripheral darkening of the optical device, non-uniformity of sensitivity of an imaging element or the like causes mismatching between an original luminance of the image and a video signal and a peripheral region of the image becomes darker than a central region.

Further, the luminance unevenness described above includes also a black area (also called vignetting) that is caused by blocking light to be condensed by part of a structure of the optical device. In this manner, in capturing of a biological image, luminance unevenness arising from various characteristics relating to the optical device may occur.

However, in general exposure control relating to a biological image, it is the current situation that such luminance unevenness arising from an optical device described above is not taken into consideration sufficiently. Therefore, the degree of separation relating to a luminance value histogram cannot be calculated correctly due to an influence of a high-luminance imaging object or the like in a biological image, and also there is a possibility that the accuracy of exposure control may degrade.

The present technical idea has been conceptualized paying attention to the point described above and implements flexible and more highly accurate exposure control that does not rely upon a characteristic of an optical device. To this end, in the surgical controlling device, control method, surgical system and program according to an embodiment of the present disclosure as one of features thereof on the basis of information regarding an identified surgical optical device (hereinafter referred to also merely as optical device), the luminance detection value is corrected so as to correct luminance unevenness arising from the surgical optical device, and then exposure control relating to capturing of a biological image is performed. With the feature just described according to the present technical idea, highly accurate automatic exposure control that does not rely upon a characteristic of the optical device can be implemented. Consequently, the cost for exposure control can be reduced, and a clearer biological image can be acquired.

2. Example of Application

Now, an example of application of the technical idea according to the present disclosure is described. FIG. 1 is a view depicting an example of manner of surgical operation to which an operating room system 5100 that uses the technical idea according to the present disclosure is applied. A ceiling camera 5187 and a surgical camera 5189 are provided on the ceiling of an operating room such that they can image a manner of the entire operating room and the hands of a surgeon (doctor) 5181 who performs treatment to the affected area of a patient 5185 on a patient bed 5183. In the ceiling camera 5187 and the surgical camera 5189, a magnification adjustment function, a focal distance adjustment function, an imaging direction adjustment function, and so forth can be provided. An illumination 5191 is provided on the ceiling of the operating room and illuminates at least the hands of the surgeon 5181. The illumination 5191 may be suitably adjustable in regard to the irradiation light amount, wavelength (color) of the irradiation light, irradiation direction of the light, and so forth.

As depicted in FIG. 1, an endoscopic surgery system 5113 and the patient bed 5183, ceiling camera 5187, surgical camera 5189 and illumination 5191 are connected in cooperation with each other through an audiovisual controller 5107 and an operating room controlling device 5109 (not depicted in FIG. 1). In the operating room, a central control panel 5111 is provided, and as described above, a user can suitably operate various devices existing in the operating room through the central control panel 5111.

In the following, a configuration of the endoscopic surgery system 5113 is described in detail. As depicted in FIG. 1, the endoscopic surgery system 5113 includes an endoscope 5115, other surgical tools 5131, a supporting arm device 5141 for supporting the endoscope 5115, and a cart 5151 on which various devices for endoscopic operation are mounted.

In endoscopic surgery, in place of cutting the abdominal wall and opening, a plurality of opening devices called trockers 5139a to 5139d punctures the abdominal wall. Then, through the trockers 5139a to 5139d, a lens barrel 5117 of the endoscope 5115 and other surgical tools 5131 are inserted into the body cavity of the patient 5185. In the example depicted, as the other surgical tools 5131, an insufflation tube 5133, an energy treatment tool 5135 and a forceps 5137 are inserted in the body cavity of the patient 5185. Further, the energy treatment tool 5135 is a treatment tool that performs incision and detachment of the tissue, sealing of a blood vessel, or the like by high-frequency current and ultrasonic vibration. However, the surgical tools 5131 depicted are merely an example, and as the surgical tools 5131, various surgical tools that are used generally in endoscopic operation such as, for example, a tweezers or a retractor may be used.

An image of an operative part in the body cavity of the patient 5185 captured by the endoscope 5115 is displayed on a display device 5155. While watching the operative part displayed on the display device 5155 on the real time basis, the surgeon 5181 performs such treatment, for example, as removal of the affected area using the energy treatment tool 5135 or the forceps 5137. It is to be noted that, though not depicted, during surgical operation, the insufflation tube 5133, energy treatment tool 5135 and forceps 5137 are supported by the surgeon 5181, an assistant, or the like.

(Supporting Arm Device)

The supporting arm device 5141 includes an arm portion 5145 extending from a base portion 5143. In the example depicted, the arm portion 5145 includes joints 5147a, 5147b, and 5147c and links 5149a and 5149b and is driven under the control of an arm controlling device 5159. The endoscope 5115 is supported by the arm portion 5145, so that the position and the posture thereof are controlled. Consequently, stable fixation of the position of the endoscope 5115 can be implemented.

(Endoscope)

The endoscope 5115 includes the lens barrel 5117 that is inserted at a region having a predetermined length from a distal end thereof into the body cavity of the patient 5185, and a camera head 5119 connected to a proximal end of the lens barrel 5117. Here, the endoscope 5115 may be an example of an optical device according to an embodiment of the present disclosure. In other words, the endoscope 5115 can be applied as an imaging device 10 hereinafter described. It is to be noted that, while, in the example depicted, the endoscope 5115 is depicted which is configured as a so-called rigid mirror having the lens barrel 5117 that is rigid, the endoscope 5115 may be configured otherwise as a flexible mirror having the flexible lens barrel 5117.

An opening in which an objective lens is fitted is provided at a distal end of the lens barrel 5117. A light source device 5157 is connected to the endoscope 5115 such that light generated by the light source device 5157 is guided to the distal end of the lens barrel 5117 by a light guide extending in the inside of the lens barrel 5117 and irradiated toward an observation target in the body cavity of the patient 5185 through the objective lens. It is to be noted that the endoscope 5115 may be a direct view mirror or may be a perspective mirror or a side view mirror.

In the inside of the camera head 5119, an optical system and an imaging element are provided, so that reflected light (observation light) from an observation target is condensed to the imaging element by the optical system. Observation light is photoelectrically converted by the imaging element to generate an electric signal corresponding to the observation light, namely, an image signal corresponding to the observation image. The image signal is transmitted as RAW data to a camera control unit (CCU) 5153. It is to be noted that the camera head 5119 has incorporated therein a function of adjusting the magnification and the focal distance by suitably driving the optical system.

It is to be noted the camera head 5119 may include a plurality of imaging elements, for example, in order to cope with a stereo vision (3D display) or the like. In this case, in the inside of the lens barrel 5117, a plurality of series of relay optical systems is provided so as to individually guide observation light to the plurality of imaging elements.

(Various Devices Carried on Cart)

The CCU 5153 includes a CPU (Central Processing Unit), a GPU (Graphics Processing Unit), and so forth and comprehensively controls operation of the endoscope 5115 and the display device 5155. Specifically, the CCU 5153 performs, for an image signal received from the camera head 5119, various image processes for displaying an image based on the image signal such as, for example, a development process (demosaic process). Further, the CCU 5153 may have a function of performing exposure control relating to capturing of a biological image by the endoscope 5115. Thereupon, the CCU 5153 identifies the endoscope 5115 or the light source device 5157 connected thereto and can correct the luminance detection value relating to the biological image in response to a characteristic of the endoscope 5115 or the light source device 5157. The CCU 5153 can be applied as an example of a control device 30 hereinafter described.

Further, the CCU 5153 provides an image signal for which the image processes are performed to the display device 5155. Further, to the CCU 5153, the audiovisual controller 5107 depicted in FIG. 1 is connected. The CCU 5153 provides the image signal for which the image processes are performed also to the audiovisual controller 5107. Further, the CCU 5153 transmits a control signal to the camera head 5119 to control driving of the camera head 5119. The control signal may include information relating to an imaging condition such as a magnification or a focal distance. The information relating to an imaging condition may be inputted through an inputting device 5161 or may be inputted through the central control panel 5111 described hereinabove.

The display device 5155 displays an image based on the image signal, for which the image processes are performed by the CCU 5153, under the control of the CCU 5153. In the case where the endoscope 5115 is compatible with imaging with a high resolution such as, for example, 4K (horizontal pixel number 3840×vertical pixel number 2160) or 8K (horizontal pixel number 7680×vertical pixel number 4320), and/or in the case where the endoscope 5115 is compatible with 3D display, as the display device 5155, a display device capable of displaying with a high resolution and/or a display device capable 3D displaying in a corresponding relationship can be used. In the case where the display device 5155 can be used for imaging of a high resolution of 4K, 8K or the like, using a display device of a size of 55 inches or more as the display device 5155 provides a more immersive feeling. Further, a plurality of display devices 5155 having resolutions or sizes different from each other may be provided depending on a use.

The light source device 5157 includes a light source such as, for example, an LED (light emitting diode) and supplies irradiation light upon imaging of an operative part to the endoscope 5115. It is to be noted that the light source device 5157 is an example of an optical device according to an embodiment of the present disclosure. The light source device 5157 can be applied as an example of an irradiation device 20 hereinafter described.

The arm controlling device 5159 includes a processor such as, for example, a CPU and operates in accordance with a predetermined program to control driving of the arm portion 5145 of the supporting arm device 5141 in accordance with a predetermined control method.

The inputting device 5161 is an input interface to the endoscopic surgery system 5113. The user can perform inputting of various kinds of information or instruction inputting to the endoscopic surgery system 5113 through the inputting device 5161. For example, the user would input various kinds of information relating to surgical operation such as physical information of a patient, information regarding surgical technique, and so forth through the inputting device 5161. Further, for example, the user would input an instruction to drive the arm portion 5145, an instruction to change an imaging condition (type of irradiation light, magnification, focal distance, or the like) by the endoscope 5115, an instruction to drive the energy treatment tool 5135, or other instructions through the inputting device 5161.

The type of the inputting device 5161 is not restrictive, and the inputting device 5161 may be any of various known inputting devices. As the inputting device 5161, for example, a mouse, a keyboard, a touch panel, a switch, a foot switch 5171 and/or a lever may be applied. In the case where a touch panel is used as the inputting device 5161, the touch panel may be provided on a display face of the display device 5155.

As an alternative, the inputting device 5161 is a device mounted on a user such as, for example, a glasses type wearable device or an HMD (Head Mounted Display), and various inputs are performed in response to gestures or gazes detected by such devices. Further, the inputting device 5161 includes a camera that can detect a movement of a user, and various inputs are performed in accordance with a gesture or a gaze of a user detected from a video captured by the camera. Furthermore, the inputting device 5161 includes a microphone that can collect voice of a user, and various inputs are performed by voice through the microphone. In this manner, the inputting device 5161 is configured so as to be capable of inputting various kinds of information in a non-contact manner, so that it is possible for a user (for example, the surgeon 5181) who belongs particularly in a clean area to operate equipment belonging to an unclean area in a non-contact manner. Further, since it becomes possible for the user to operate the equipment without removing a hand from a grasped tool, the convenience to the user is improved.

A treatment tool controlling device 5163 controls driving of the energy treatment tool 5135 for cauterization or incision of the tissue, sealing of a blood vessel or the like. An insufflation device 5165 feeds gas into the body cavity of the patient 5185 through the insufflation tube 5133 to inflate the body cavity in order to secure a field of view by the endoscope 5115 and secure a work space of the operator. A recorder 5167 is a device capable of recording various kinds of information relating to surgical operation. A printer 5169 is a device capable of printing various kinds of information relating to surgical operation in various forms such as a text, an image, or a graph.

In the following, a characteristic configuration of the endoscopic surgery system 5113 is specifically described in more detail.

(Supporting Arm Device)

The supporting arm device 5141 includes the base portion 5143 serving as a base, and the arm portion 5145 extending from the base portion 5143. Although, in the example depicted, the arm portion 5145 includes a plurality of joints 5147a, 5147b and 5147c and a plurality of links 5149a and 5149b connected to each other by the joint 5147b, in FIG. 1, for simplicity, the configuration of the arm portion 5145 is displayed in a simplified form. Actually, the shape, number and arrangement of the joints 5147a to 5147c and the links 5149a and 5149b and the direction of the axis of rotation and so forth of the joints 5147a to 5147c can be suitably set such that the arm portion 5145 has a desired degree of freedom. For example, the arm portion 5145 can be suitably configured in such a way as to have six or more degrees of freedom. Since this makes it possible for the endoscope 5115 to freely move in a movable range of the arm portion 5145, it becomes possible to insert the lens barrel 5117 of the endoscope 5115 from a desired direction into the body cavity of the patient 5185.

An actuator is provided for each of the joints 5147a to 5147c, and the joints 5147a to 5147c are configured for rotation around respective predetermined axes of rotation by driving the actuators. Since driving of the actuators is controlled by the arm controlling device 5159, the rotational angles of the joints 5147a to 5147c are controlled, and driving of the arm portion 5145 is controlled. Consequently, control of the position and the posture of the endoscope 5115 can be implemented. Thereupon, the arm controlling device 5159 can control driving of the arm portion 5145 by various known control methods such as force control or position control.

For example, when the surgeon 5181 suitably performs operation inputting through the inputting device 5161 (including the foot switch 5171), driving of the arm portion 5145 may be suitably controlled by the arm controlling device 5159 in response to the operation input to control the position and the posture of endoscope 5115. After the endoscope 5115 at the distal end of the arm portion 5145 is moved from an arbitrary position to another arbitrary position, the endoscope 5115 can be supported fixedly at the position after the movement by the control described above. It is to be noted that the arm portion 5145 may be operated by a so-called master-slave method. In this case, the arm portion 5145 can be remotely operated by the user through the inputting device 5161 installed at a place spaced from the operating room.

Also, in the case where force control is applied, the arm controlling device 5159 may receive external force from the user and perform so-called power assist control for driving the actuators of the joints 5147a to 5147c such that the arm portion 5145 moves smoothly following the external force. Consequently, when the user moves the arm portion 5145 while directly touching with the arm portion 5145, the arm portion 5145 can be moved with comparatively light force. Accordingly, it is possible to move the endoscope 5115 more intuitively by a simpler operation, so that the convenience to the user can be improved.

Here, in general, in endoscopic operation, the endoscope 5115 has been supported by a doctor called a scopist. In contrast, by using the supporting arm device 5141, it becomes possible to fix the position of the endoscope 5115 more surely without hands, and therefore, an image of the operative part can be obtained stably, and surgical operation can be performed smoothly.

It is to be noted that the arm controlling device 5159 may not necessarily be provided on the cart 5151. Further, the arm controlling device 5159 may not necessarily be a single device. For example, the arm controlling device 5159 may be provided on each of the joints 5147a to 5147c of the arm portion 5145 of the supporting arm device 5141 such that the plurality of arm controlling devices 5159 may cooperate with each other to implement driving control of the arm portion 5145.

(Light Source Device)

The light source device 5157 supplies irradiation light when an operative part is to be imaged to the endoscope 5115. The light source device 5157 includes, for example, a white light source configured from an LED, a laser light source or a combination of them. At this time, in the case where a white light source includes a combination of RGB laser light sources, since the output intensity and the output timing of each color (each wavelength) can be controlled with high accuracy, adjustment of the white balance of a captured image can be performed by the light source device 5157. Further, in this case, laser beams are irradiated time-divisionally from the respective RGB laser light sources upon an observation target, and driving of the imaging element of the camera head 5119 is controlled in synchronism with the irradiation timing, so that it is also possible to time-divisionally capture images individually corresponding to RGB colors. According to the method just described, a color image can be obtained even if color filters are not provided in the imaging element.

Further, the light source device 5157 may be controlled for driving such that the intensity of light to be outputted is changed for each predetermined period of time. Driving of the imaging element of the camera head 5119 is controlled in synchronism with the timing of the change of the intensity of light to time-divisionally obtain images and synthesize the images, so that an image of a high dynamic range free from so-called underexposed blocked up shadows and overexposed highlights can be created.

Further, the light source device 5157 may be configured such that it can supply light of a predetermined wavelength band ready for special light observation. In the special light observation, by applying light of a narrow band in comparison with irradiation light (that is, white light) upon normal observation utilizing the wavelength dependency of absorption of light by the body tissue, for example, so-called narrow band light observation (Narrow Band Imaging) of imaging a predetermined tissue such as a blood vessel of the mucosal surface with high contrast is performed. Otherwise, in the special light observation, fluorescence observation of obtaining an image using fluorescence generated by applying excitation light may be performed. In the fluorescence observation, fluorescence observation of applying excitation light upon the body tissue and observing fluorescence from the body tissue (autofluorescence observation) or fluorescence observation of locally injecting reagent such as indocyanine green (ICG) and applying excitation light corresponding to a fluorescence wavelength of the reagent to the body tissue to obtain a fluorescence image, for example, can be performed. The light source device 5157 can be configured to be able to supply narrow band light and/or excitation light compatible with such special light observation.

Figure 2:
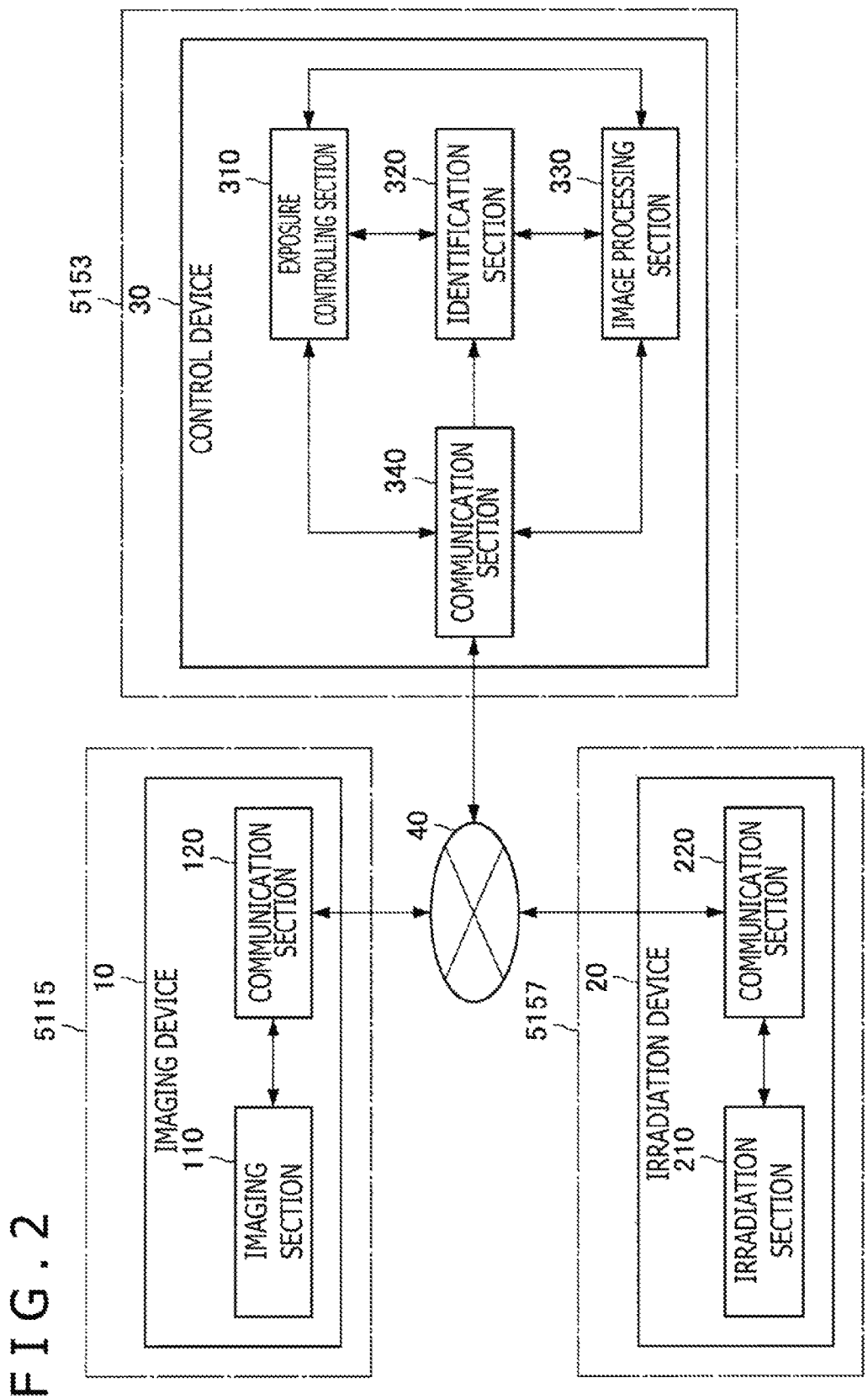
FIG. 2 is an example of a functional block diagram of a surgical system according to an embodiment the present disclosure.

3. Embodiment 3.1. Example of System Configuration and Example of Functional Configuration Now, an embodiment of the present disclosure is described. First, described are an example of a configuration of a surgical system according to an embodiment of the present disclosure and an example of a functional configuration of components of the surgical system. FIG. 2 is an example of a functional block diagram of the surgical system according to the present embodiment. Referring to FIG. 2, the surgical system according to the present embodiment may include an imaging device 10, an irradiation device 20, and a control device 30. Further, the imaging device 10, irradiation device 20, and control device 30 are connected to each other so as to communicate with each other through a network 40.

(Imaging Device 10)

The imaging device 10 according to the present embodiment is a surgical imaging device for capturing a biological image in the body cavity of an observation object. As described hereinabove, the imaging device 10 according to the present embodiment is an example of a surgical optical device. Further, the imaging device 10 according to the present embodiment may be, for example, the endoscope 5115 depicted in FIG. 1. Further, the imaging device 10 according to the present embodiment includes an imaging section 110 and a communication section 120 as depicted in FIG. 2.

((Imaging Section 110))

The imaging section 110 has a function of capturing a biological image in the body cavity of an observation object. Thereupon, the imaging section 110 may perform capturing of a biological image under the exposure control of the control device 30. The imaging section 110 can perform capturing of a biological image using a shutter speed or a gain based on a control signal generated, for example, by the control device 30.

The imaging section 110 according to the present embodiment is configured including an imaging element such as, for example, a CCD (Charge Coupled Device) or a CMOS (Complementary MOS). Here, such biological images according to the present embodiment widely include images acquired from a biological point of view for clinical, medical and experimental uses (Biological Imaging), and the imaging object is not limited to a human.

((Communication Section 120))

The communication section 120 has a function of performing information communication with the irradiation device 20 or the control device 30 through the network 40. Specifically, the communication section 120 transmits a captured biological image or identification information for specifying the imaging device 10 to the control device 30. Here, the identification information may be an ID capable of specifying, for example, a model of the imaging device 10. Further, the communication section 120 receives a control signal relating to exposure control from the control device 30. The communication section 120 may receive a control signal, for example, relating to a shutter speed or gain setting from the control device 30.

(Irradiation Device 20)

The irradiation device 20 according to the present embodiment has a function of providing irradiation light to be used for capturing of a biological image. As described hereinabove, the irradiation device 20 according to the present embodiment is an example of a surgical optical device. Further, the irradiation device 20 according to the present embodiment may be, for example, the light source device 5157 depicted in FIG. 1. Further, the irradiation device 20 according to the present embodiment includes an irradiation section 210 and a communication section 220 as depicted in FIG. 2.

((Irradiation Section 210))

The irradiation section 210 is configured including, for example, a light source and a condenser lens. The irradiation section 210 may have a function of condensing light emitted from a light source on the imaging device 10. Light emitted from the light source of the irradiation section 210 is guided to a distal end of the lens barrel 5117 of the endoscope 5115, for example, by a light guide extending in the inside of the lens barrel and is irradiated toward an observation target in the body cavity of the patient 5185 through the objective lens.

((Communication Section 220))

The communication section 220 has a function of performing information communication with the imaging device 10 or the control device 30 through the network 40. Specifically, the communication section 220 transmits identification information for specifying the irradiation device 20 to the control device 30. Here, the identification information described above may be an ID with which, for example, a model of the irradiation device 20 or the like can be specified.

(Control Device 30)

The control device 30 according to the present embodiment is a surgical controlling device performing exposure control relating to capturing a biological image. Thereupon, the control device 30 according to the present embodiment has a function of correcting a luminance detection value regarding a biological image in accordance with the identified surgical optical device. It is to be noted that, as an example of the surgical optical device according to the present embodiment, the imaging device 10 and the irradiation device 20 described hereinabove are available. Further, the surgical optical device according to the present embodiment is not limited to such an example as just described and may include various types of surgical optical devices relating to capturing of a biological image, such as the irradiation type, light collecting type and image forming type. Further, the control device 30 according to the present embodiment may be, for example, the CCU 5153 depicted in FIG. 1. The control device 30 according to the present embodiment includes an exposure controlling section 310, an identification section 320, an image processing section 330, and a communication section 340 as depicted in FIG. 2.

((Exposure Controlling Section 310))

The exposure controlling section 310 has a function of performing exposure control relating to capturing of a biological image. The exposure controlling section 310 can perform exposure control on the basis of comparison, for example, between a luminance detection value (hereinafter referred to as reference) defined as an appropriate level and a detected luminance detection value. Specifically, in the case where the detected luminance detection value is higher than the reference, the exposure controlling section 310 performs control of increasing the shutter speed from a speed at present or decreasing the gain from a gain at present, and accordingly, it is possible to decrease the exposure light amount thereby to control the luminance detection value so as to have a level same as that of the reference.

In contrast, in the case where the detected luminance detection value is lower than the reference, the exposure controlling section 310 performs control of reducing the shutter speed from that at present or increasing the gain from that at present, accordingly, it is possible to increase the exposure light amount thereby to control the luminance detection value so as to have a level same as that of the reference.

Further, one of features of the exposure controlling section 310 according to the present embodiment is that exposure control based on a luminance detection value detected from a biological image is performed. In this case, the exposure controlling section 310 according to the present embodiment has another one of the features that the luminance detection value in the biological image is corrected such that luminance unevenness arising from the identified surgical optical device is corrected. More specifically, the exposure controlling section 310 can specify a luminance correction value for correcting luminance unevenness arising from a surgical optical device and perform correction of the luminance detection value relating to the biological image using the luminance correction value. According to the functions of the exposure controlling section 310 according to the present embodiment described above, the luminance unevenness by a characteristic of the surgical optical device is absorbed, and then, it is possible to perform exposure control with high accuracy.

It is to be noted that, as described hereinabove, the luminance unevenness according to the present embodiment may include shading or a black area arising from a surgical optical device. In other words, the exposure controlling section 310 according to the present embodiment can correct a luminance detection value regarding a biological image using a luminance correction value for correcting a luminance variation arising from shading or a black area generated by a characteristic of the imaging device 10 or the irradiation device 20.

Thereupon, the exposure controlling section 310 according to the present embodiment may detect an imaging object having a luminance equal to or higher than a predetermined threshold value (hereinafter referred to also as high luminance imaging object) in a biological image and perform correction of a luminance detection value using a luminance correction value corresponding to the position of the imaging object in the biological image. More specifically, the exposure control according to the present embodiment can calculate the distance from the center of the biological image to the imaging object and correct the luminance detection value using a luminance correction value corresponding to the distance. Details of the functions of the exposure controlling section 310 according to the present embodiment are hereinafter described separately.

((Identification Section 320))

The identification section 320 has a function of identifying a surgical optical device. The identification section 320 according to the present embodiment may perform the identification described above on the basis of identification information received, for example, from the imaging device 10 or the irradiation device 20. Also, for example, the identification section 320 according to the present embodiment may identify the imaging device 10 on the basis of a biological image captured by the imaging device 10. Further, the identification section 320 may perform recognition of an optical device on the basis of information inputted, for example, by the surgeon.

Further, the identification section 320 according to the present embodiment has a function of identifying the direction of the imaging device 10. The identification section 320 can identify the direction of the imaging device 10 on the basis of a biological image captured by the imaging device 10, for example. Further, the identification section 320 may identify the direction of the imaging device 10 on the basis of sensor information collected from the imaging device 10 or other peripheral apparatus. According to the functions described above of the identification section 320, the exposure controlling section 310 can correct a luminance detection value relating to a biological image in accordance with the direction of the surgical optical device.

((Image Processing Section 330))

The image processing section 330 has a function of performing various image processes for a biological image captured by the imaging device 10. The image processing section 330 according to the present embodiment may perform, for example, a gradation conversion process or a noise reduction process.

((Communication Section 340))

The communication section 340 has a function of performing information communication with the imaging device 10 or the irradiation device 20 through the network 40. Specifically, the communication section 340 receives a biological image and identification information for specifying the imaging device 10 from the imaging device 10. Further, the communication section 340 receives identification information for specifying the irradiation device 20 from the irradiation device 20. Thereupon, the communication section 340 may acquire identification information relating to the irradiation device 20 through the imaging device 10. Further, the communication section 340 transmits a control signal relating to exposure control generated by the exposure controlling section 310 to the imaging device 10. As described above, the control signal described above can include a signal relating to control of the shutter speed or gain setting.

3.2. Details of Correction of Luminance Detection Value

Now, correction of a luminance detection value by the exposure controlling section 310 according to the present embodiment is described in detail. As described hereinabove, the exposure controlling section 310 according to the present embodiment can implement exposure control with high accuracy that does not rely upon an optical device by correcting luminance unevenness arising from a characteristic of the optical device.

Figure 3:
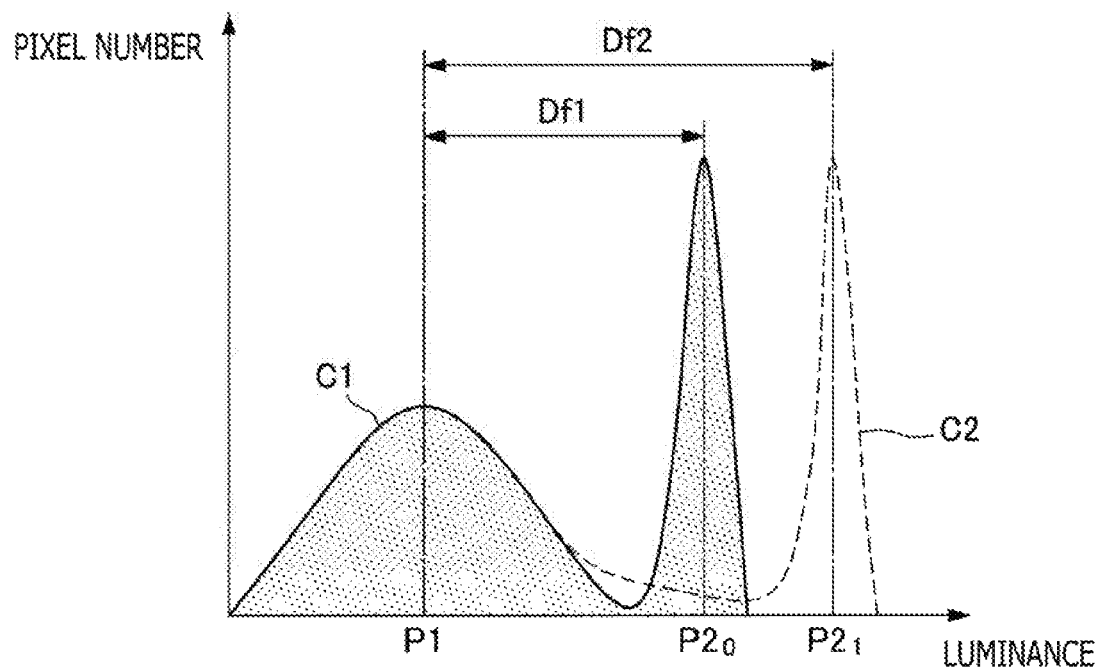
FIG. 3 is a view illustrating luminance unevenness arising from a characteristic of an optical device according to the embodiment.

First, luminance unevenness arising from a characteristic of an optical device is described. FIG. 3 is a view illustrating luminance unevenness arising from a characteristic of an optical device according to the present embodiment. FIG. 3 depicts a luminance value histogram generated on the basis of luminance detection values obtained from a plurality of detection frames set to a biological image. It is to be noted that, in the luminance value histogram depicted in FIG. 3, the luminance value is indicated on the axis of abscissa and the pixel number is indicated on the axis of ordinate.

Further, in FIG. 3, a luminance value histogram by two curves C1 and C2 is indicated. Here, the curve C1 represents a luminance value histogram in the case where, in a state in which such luminance unevenness as shading arising from an optical device, namely, from the imaging device 10 or the irradiation device 20 occurs, a high-luminance imaging object exists in a peripheral portion of the biological image. Meanwhile, the curve C2 represents a luminance value histogram in the case of a state in which such luminance unevenness as shading arising from the imaging device 10 or the irradiation device 20 does not occur or in the case where a high-luminance imaging object exists in a central region in which the influence of luminance unevenness is small.

As described above, according to an example of the technique for exposure control, although it is possible to perform exposure control on the basis of the degree of separation of peak medians in the generated luminance value histogram, referring to FIG. 3, it can be recognized that a difference occurs in degree of separation described above due to luminance unevenness arising from the optical device.

More in detail, it becomes clear that the degree Df1 of separation obtained from peak medians P1 and $P2_0$ detected on the curve C1 with which luminance unevenness occurs is small in comparison with the degree Df2 of separation obtained from peak medians P1 and $P2_1$ detected on the curve C2 with which no luminance unevenness occurs.

Since luminance unevenness arising from a characteristic of an optical device has a significant influence on the peak median or the degree of separation of a luminance value histogram in this manner, it may cause accuracy degradation in exposure control based on the degree of separation.

Therefore, the exposure controlling section 310 according to the present embodiment can exclude the influence of luminance unevenness arising from an optical device by correcting a luminance detection value regarding a biological image using a luminance correction value compatible with the imaging device 10 or the irradiation device 20 identified by the identification section 320.

Thereupon, the exposure controlling section 310 according to the present embodiment may detect a high-luminance imaging object in the biological image and perform correction of the luminance detection value using the luminance correction value according to the distance from the center of the biological image to the high-luminance imaging object.

Figure 4:
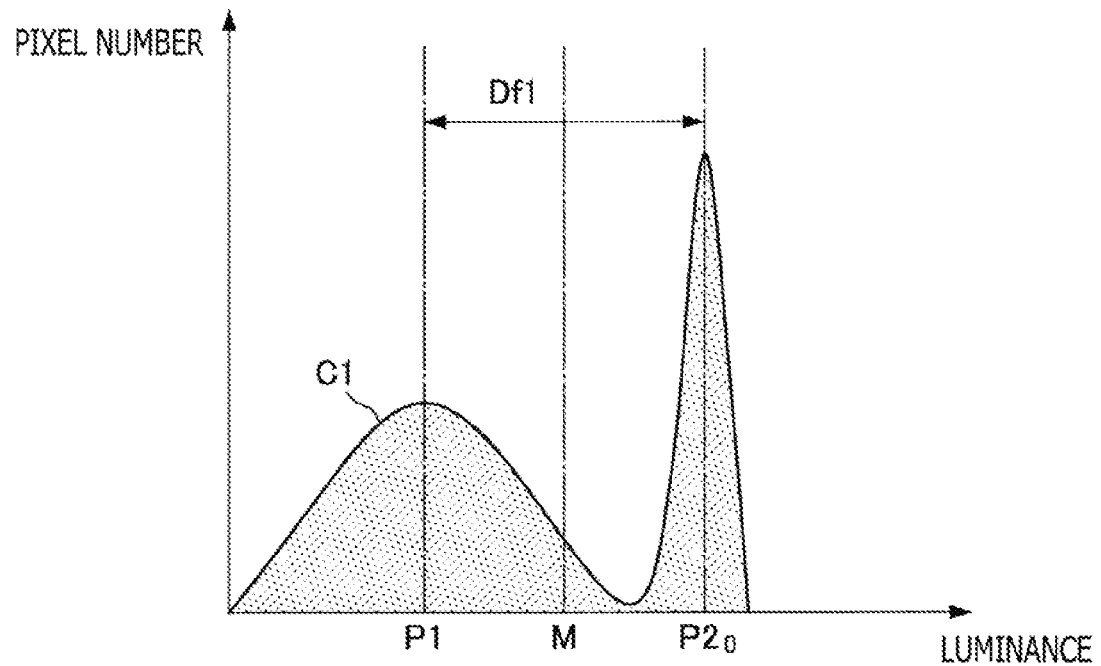
FIG. 4 is a view illustrating detection of a high-luminance imaging object according to the embodiment.

FIG. 4 is a view illustrating detection of a high-luminance imaging object according to the present embodiment. In FIG. 4, a luminance histogram generated by the exposure controlling section 310 on the basis of luminance detection values regarding a biological image is depicted similarly as in FIG. 3. Thereupon, the exposure controlling section 310 may calculate a center value M of a degree Df1 of separation obtained from the peak medians P1 and $P2_0$ to perform detection of a high-luminance imaging object. More specifically, in the case where a luminance detection value of a detection frame set to a biological image is equal to or higher than the center value M of the degree of separation, the exposure controlling section 310 can detect the detection frame as a high-luminance detection frame, namely, as a high-luminance imaging object.

Further, the exposure controlling section 310 according to the present embodiment may calculate the distance from the center of the biological image to the high-luminance detection frame (hereinafter referred to simply as high-luminance imaging object) and perform correction of the luminance detection value using a luminance correction value according to the distance.

Figure 5:
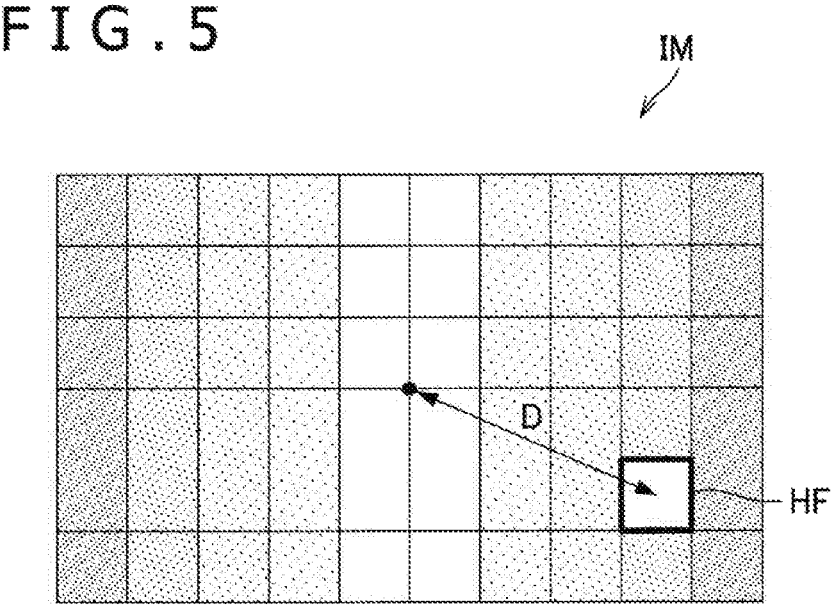
FIG. 5 is a view illustrating calculation of a distance from the center of a biological image to a high-luminance imaging object by an exposure controlling section according to the embodiment.

FIG. 5 is a view illustrating calculation of a distance from the center of a biological image to a high-luminance imaging object by the exposure controlling section 310 according to the present embodiment. In FIG. 5, a plurality of detection frames set to a biological image IM and a high-luminance imaging object HF detected on the basis of the center value of the degree of separation are described. Thereupon, the exposure controlling section 310 according to the present embodiment calculates the distance D from the center of the biological image IM to the high-luminance imaging object HF as depicted in FIG. 5.

Figure 6:
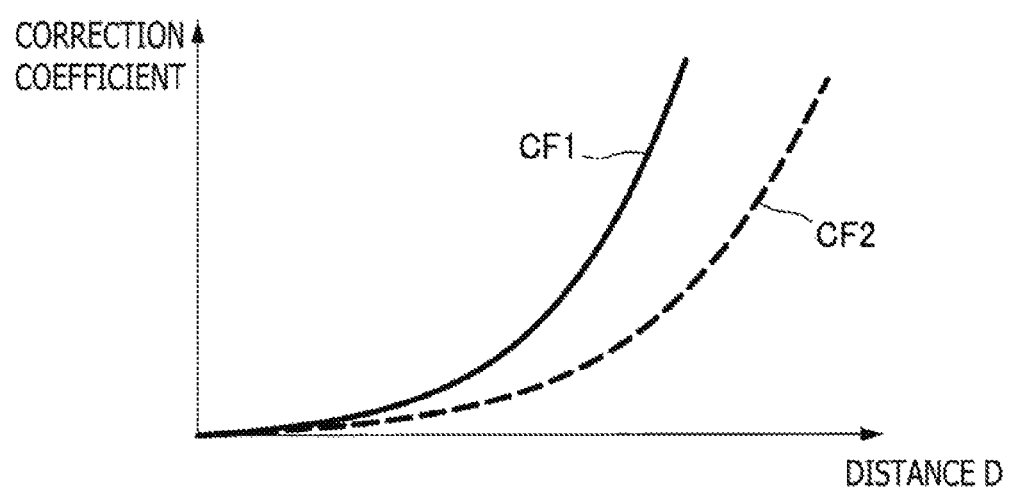
FIG. 6 is a view depicting a relationship between the distance from the center of a biological image to a high-luminance imaging object and a luminance correction value according to the embodiment.

Then, the exposure controlling section 310 acquires a luminance correction value on the basis of the calculated distance D. FIG. 6 is a view depicting a relationship between the distance from the center of a biological image to the high-luminance imaging object and a luminance correction value according to the present embodiment. In FIG. 6, the distance D from the center of a biological image to the high-luminance imaging object is indicated on the axis of abscissa and the correction coefficient is indicated on the axis of ordinate.

Further, in the example depicted in FIG. 6, luminance correction values CF1 and CF2 regarding two optical devices are depicted. Here, the luminance correction value CF1 may be a luminance correction value, for example, corresponding to a certain irradiation device 20, and the second correction value CF2 may be a luminance correction value, for example, corresponding to a certain imaging device 10. The exposure controlling section 310 according to the present embodiment may acquire a corresponding luminance correction value in response to an optical device identified by the identification section 320.

It is to be noted that, referring to FIG. 6, it can be recognized that the correction coefficient increases in accordance with the distance D in regard to both of the luminance correction values CF1 and CF2. This is because, as the distance from the center of a biological image to the high-luminance imaging object increases, the luminance detection value decreases due to luminance unevenness such as shading arising from the optical device. In other words, according to the exposure controlling section 310 according to the present embodiment, it is possible to correct the luminance, which becomes darker at peripheral portions of an image from an influence of luminance unevenness, to that in a normal state. Further, since the above-described correction by the exposure controlling section 310 according to the present embodiment is applicable also in the case where the detection range of the luminance is changed dynamically, more flexible exposure control can be implemented.

Further, the exposure controlling section 310 according to the present embodiment may perform correction of a luminance detection value using a plurality of luminance correction values individually corresponding to a plurality of optical devices. In other words, the exposure controlling section 310 according to the present embodiment can perform correction of a luminance detection value corresponding to a combination of characteristics of a plurality of optical devices.

Figure 7:
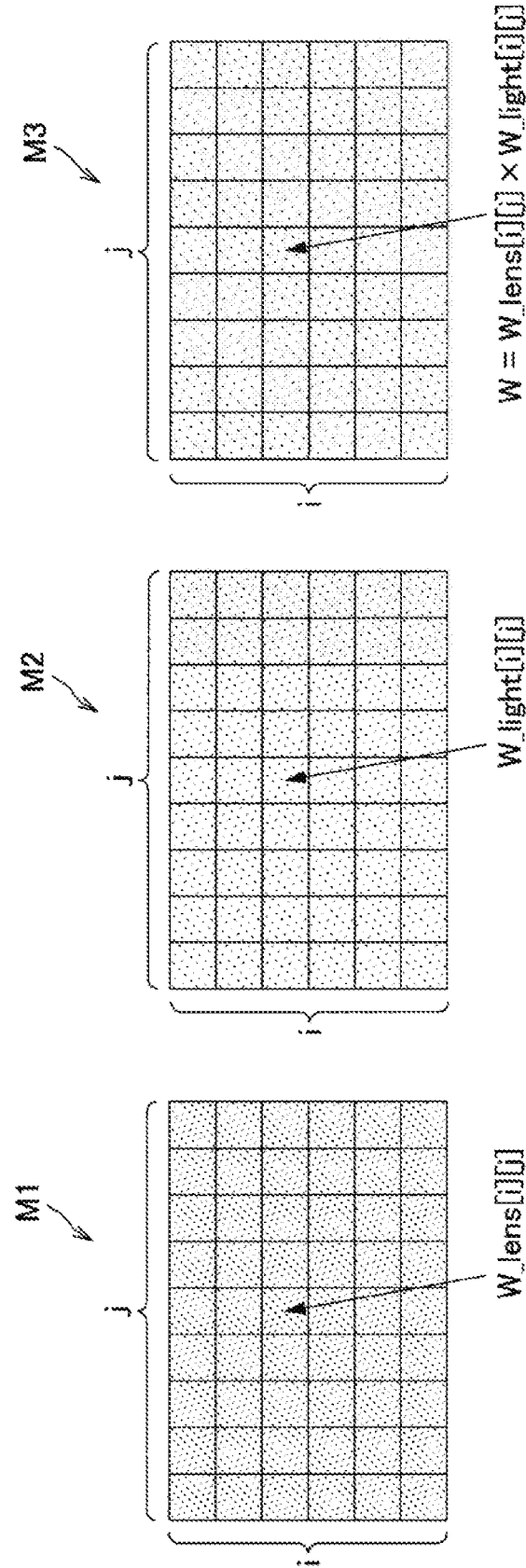
FIG. 7 is a view illustrating correction of a luminance detection value corresponding to a combination of characteristics of a plurality of optical devices by the exposure controlling section according to the embodiment.

FIG. 7 is a view illustrating correction of a luminance detection value corresponding to a combination of characteristics of a plurality of optical devices by the exposure controlling section 310 according to the present embodiment. In FIG. 7, a correction map M1 corresponding to a certain imaging device 10 and a correction map M2 corresponding to a certain irradiation device 20 as well as a synthetic correction map M3 synthesized by the exposure controlling section 310 are depicted.

Here, the correction maps M1 and M2 described above may each be a map as which a luminance correction value according to the distance D from the center of a biological image to the high-luminance imaging object is defined in advance. In other words, to each cell of the correction maps M1 and M2 depicted in FIG. 7, a correction coefficient W according to the distance D described above may individually be set.

Here, when the correction coefficient W of each cell in the correction map M1 of i rows and j columns is represented by W_lens[i][j] and the correction coefficient W of each cell in the correction map M2 of i rows and j columns is represented by W_light[i][j], then the correction coefficient W of each cell in the synthetic correction map M3 of i rows and j columns can be calculated by W=W_lens[i][j]×W_light[i][j].

That is, the exposure controlling section 310 according to the present embodiment may perform correction of a luminance detection value using a value obtained by multiplying a plurality of luminance correction values individually corresponding to a plurality of optical devices. In this manner, with the exposure controlling section 310 according to the present embodiment, correction of a luminance detection value corresponding to a combination of characteristics of a plurality of optical devices can be performed, and exposure control of high accuracy can be performed automatically also, for example, in endoscopic surgery in which a plurality of optical devices according to a use of a technique is used.

3.3. Details of Identification of Optical Device

Now, identification of an optical device by the identification section 320 according to the present embodiment is described in detail. As described hereinabove, the identification section 320 according to the present embodiment has a function of identifying various optical devices to be used for capturing of a biological image. At this time, the identification section 320 according to the present embodiment may perform identification of an optical device system on the basis of identification information transmitted from the imaging device 10 or the irradiation device 20 connected thereto through the network 40.

Figure 8:
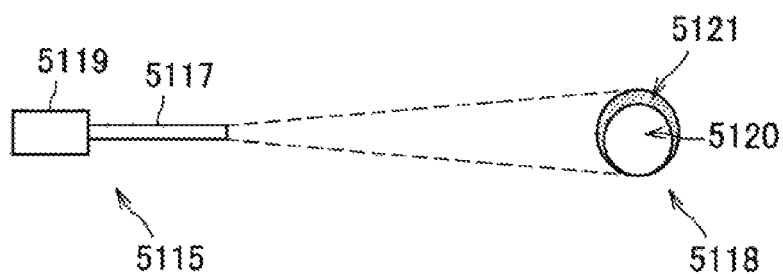
FIG. 8 is a view illustrating a shape of an imaging device and identification of the imaging device by the identification section according to the embodiment.

In addition, the identification section 320 according to the present embodiment can also perform identification of an optical device on the basis of a biological image captured by the imaging device 10. FIG. 8 is a view illustrating the shape of the imaging device 10 according to the present embodiment and identification of the imaging device 10 by the identification section 320. It is to be noted that, in FIG. 8, an example of the case in which the imaging device 10 according to the present embodiment is the endoscope 5115 is depicted.

A schematic external configuration of the endoscope 5115 according to the present embodiment is depicted on the left side in FIG. 8. As depicted in FIG. 8, the endoscope 5115 according to the present embodiment may include a camera head 5119 and a lens barrel 5117 to be inserted into the body cavity of a patient 5185. Here, for example, as depicted in FIG. 8, a light source emission port 5121 and a lens distal end portion 5120 are formed at a distal end portion 5118 of the lens barrel 5117.

At this time, while luminance blurring arising from the shape of the light source emission port 5121 appears in a biological image captured by the endoscope 5115, it is common that the shape of the light source emission port 5121 differs depending upon the manufacturer or the model of the endoscope 5115. Therefore, the identification section 320 according to the present embodiment may estimate the shape of the light source emission port 5121 from the luminance blurring in the biological image to identify the endoscope 5115.

Figure 9:
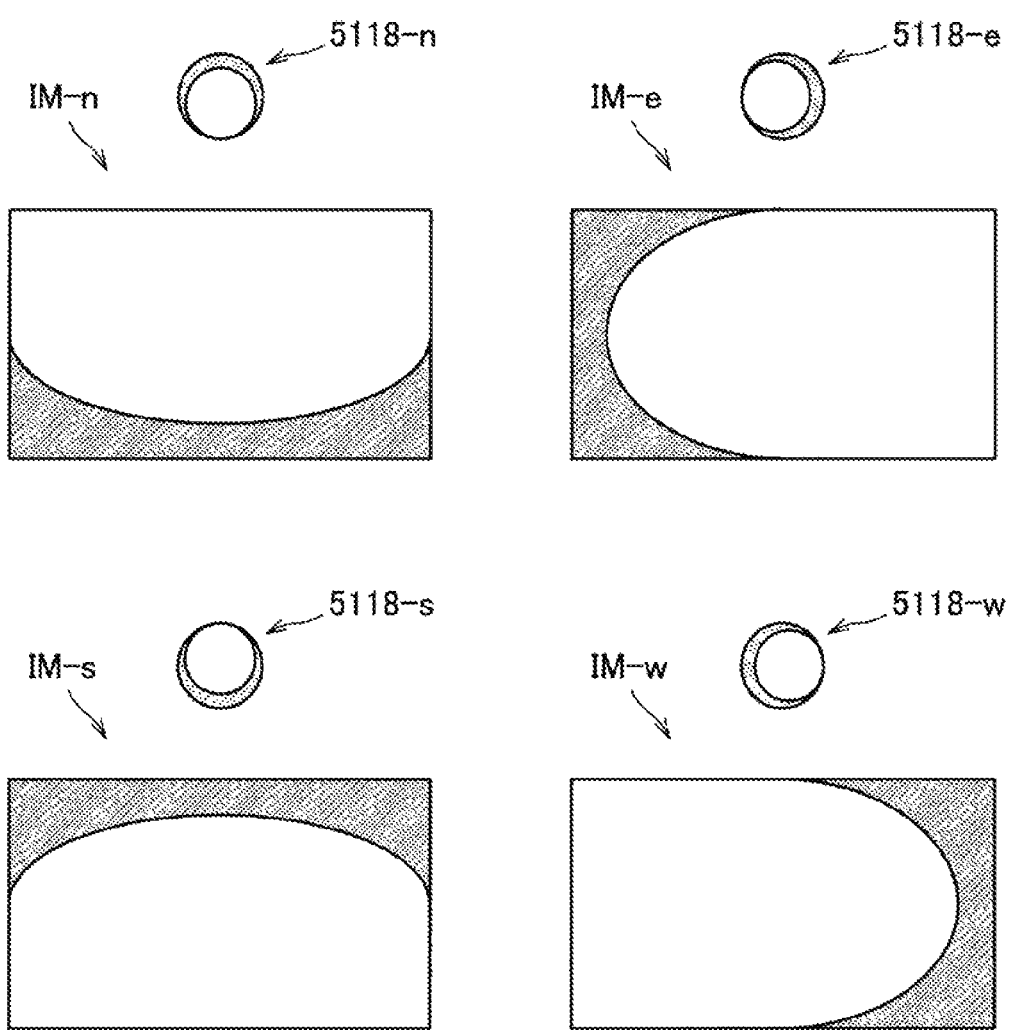
FIG. 9 is a view depicting a corresponding relationship between the direction of an endoscope and a biological image to be captured according to the embodiment.

Further, at this time, the identification section 320 according to the present embodiment can also identify the direction of the endoscope 5115 on the basis of the shape of the light source emission port 5121 pictured in the biological image. FIG. 9 is a view depicting a corresponding relationship between the direction of the endoscope 5115 according to the present embodiment and the captured biological image. In FIG. 9, distal end portions 5118-*n*, 5118-*e*, 5118-*s* and 5118-*w* of the lens barrel 5117 whose directions are different from one another and biological images IM-n, IM-e, IM-s and IM-w to be captured corresponding to the respective directions are depicted.

For example, in the case where the direction of the endoscope 5115 is in a state of a distal end portion 5110-*n* of the lens barrel 5117, in the captured biological image IM-n, the image upper side on which the light source emission port 5121 exists is brighter as depicted in FIG. 9. Similarly, in the biological image IM-e, the image right side on which the light source emission port 5121 exists is brighter; in the biological image IM-s, the image lower side on which the light source emission port 5121 exists is brighter; and in the biological image IM-w, the image left side on which the light source emission port 5121 exists is brighter.

Therefore, since high-luminance imaging objects are crowded in a predetermined direction in the captured biological image, the identification section 320 according to the present embodiment can identify the direction of the endoscope 5115. With the above-described function of the identification section 320 according to the present embodiment, the exposure controlling section 310 can use a correction map corresponding to the direction of the imaging device 10 or the like and implement exposure control with higher accuracy.

It is to be noted, while the foregoing description is given taking a case in which the identification section 320 according to the present embodiment identifies the direction of the imaging device 10 on the basis of a captured biological image as an example, identification of the direction of the imaging device 10 by the identification section 320 is not limited to that of the example. The identification section 320 according to the present embodiment may identify the direction described above, for example, on the basis of information collected by a gyroscopic sensor, a geomagnetic sensor, or the like included in the imaging device 10. Further, the identification section 320 according to the present embodiment can also identify the direction of the imaging device 10 on the basis of a magnet or the like disposed at a predetermined position of the imaging device 10 and magnetic information detected by a magnetic sensor included in a different apparatus.

3.4. Flow of Operation of Control Device

Figure 10:
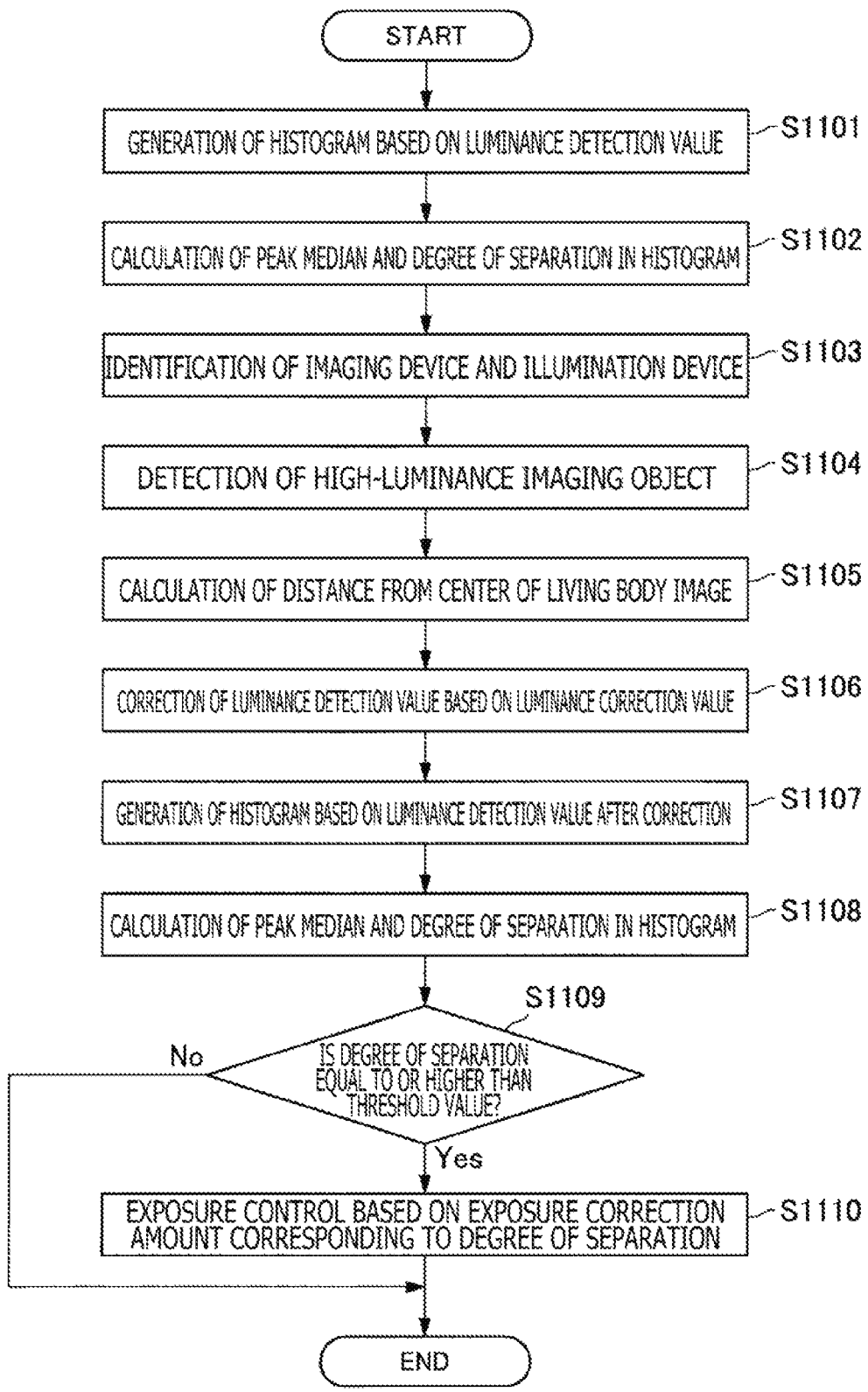
FIG. 10 is a flow chart depicting a flow of operation of the control device according to the embodiment.

Now, a flow of operation of the control device 30 according to the present embodiment is described in detail. FIG. 10 is a flow chart illustrating a flow of operation of the control device 30 according to the present embodiment. It is to be noted that operations described in the flow chart depicted in FIG. 10 may be executed for each biological image to be captured, namely, for each frame.

Referring to FIG. 10, the exposure controlling section 310 of the control device 30 first performs generation of a luminance value histogram based on luminance detection values of a biological image (S1101). Thereupon, the luminance detection values described above may be acquired in units of a plurality of detection frames as depicted in FIG. 5.

Then, the exposure controlling section 310 calculates a peak median and a degree of separation in the luminance value histogram generated at step S1101 (S1102).

Then, the identification section 320 performs identification of the imaging device 10 or the irradiation device 20 (S1103). Thereupon, as described above, the identification section 320 can perform the identification described above on the basis of the acquired identification information or biological image.

Then, the exposure controlling section 310 performs detection of a high-luminance imaging object in the biological image (S1104). At this time, as depicted in FIG. 4, the exposure controlling section 310 can perform detection of a high-luminance imaging object on the basis of the center value of the degree of separation.

Then, the exposure controlling section 310 calculate a distance from the center of the biological image in regard to the high-luminance imaging object detected at step S1104 (S1105).

Then, the exposure controlling section 310 acquires a luminance correction value corresponding to the imaging device 10 or the irradiation device 20 identified at step S1103 and performs correction of the luminance detection value (S1106). Thereupon, the exposure controlling section 310 may perform correction of the luminance detection value using, for example, such a correction map as depicted in FIG. 7.

Then, the exposure controlling section 310 performs generation of a luminance value histogram again on the basis of the luminance detection value after correction (S1107).

Then, the exposure controlling section 310 calculates a peak median and a degree of separation in the luminance value histogram generated at step S1107 (S1108).

Then, the exposure controlling section 310 determines whether or not the degree of separation calculated at step S1108 is equal to or higher than a threshold value (S1109).

Here, in the case where the degree of separation is equal to or higher than the threshold value (S1109: Yes), namely, in the case where the degree of separation between a noticed imaging object and the high-luminance imaging object is equal to or higher than the threshold value, the exposure controlling section 310 acquires an exposure correction amount corresponding to the degree of separation calculated at step S1108 and performs exposure control based on the exposure correction amount (S1110).

Figure 11:
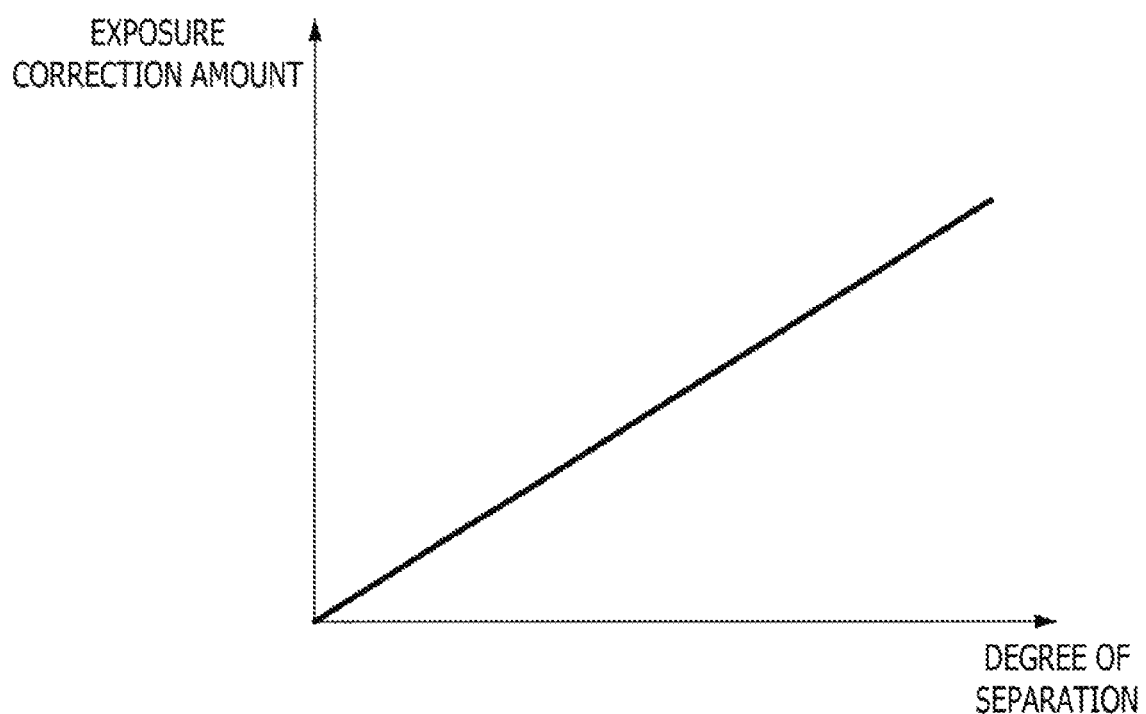
FIG. 11 is a view depicting a relationship between a degree of separation and an exposure correction amount according to the embodiment.

Thereupon, the exposure controlling section 310 may acquire the exposure correction amount described above, for example, from such a correction table as depicted in FIG. 11 and perform the exposure control. FIG. 11 is a view depicting a relationship between the degree of separation and the exposure correction amount according to the present embodiment. In order to implement the acquired exposure correction amount, the exposure controlling section 310 may generate a control signal, for example, relating to a shutter speed or gain setting and transmit the control signal to the imaging device 10 through the communication section 340.

In contrast, in the case where the degree of separation is lower than the threshold value (S1109: No), the control device 30 may move to a process for a next biological image without executing the exposure control at step S1110.

4. Example of Hardware Configuration

Figure 12:
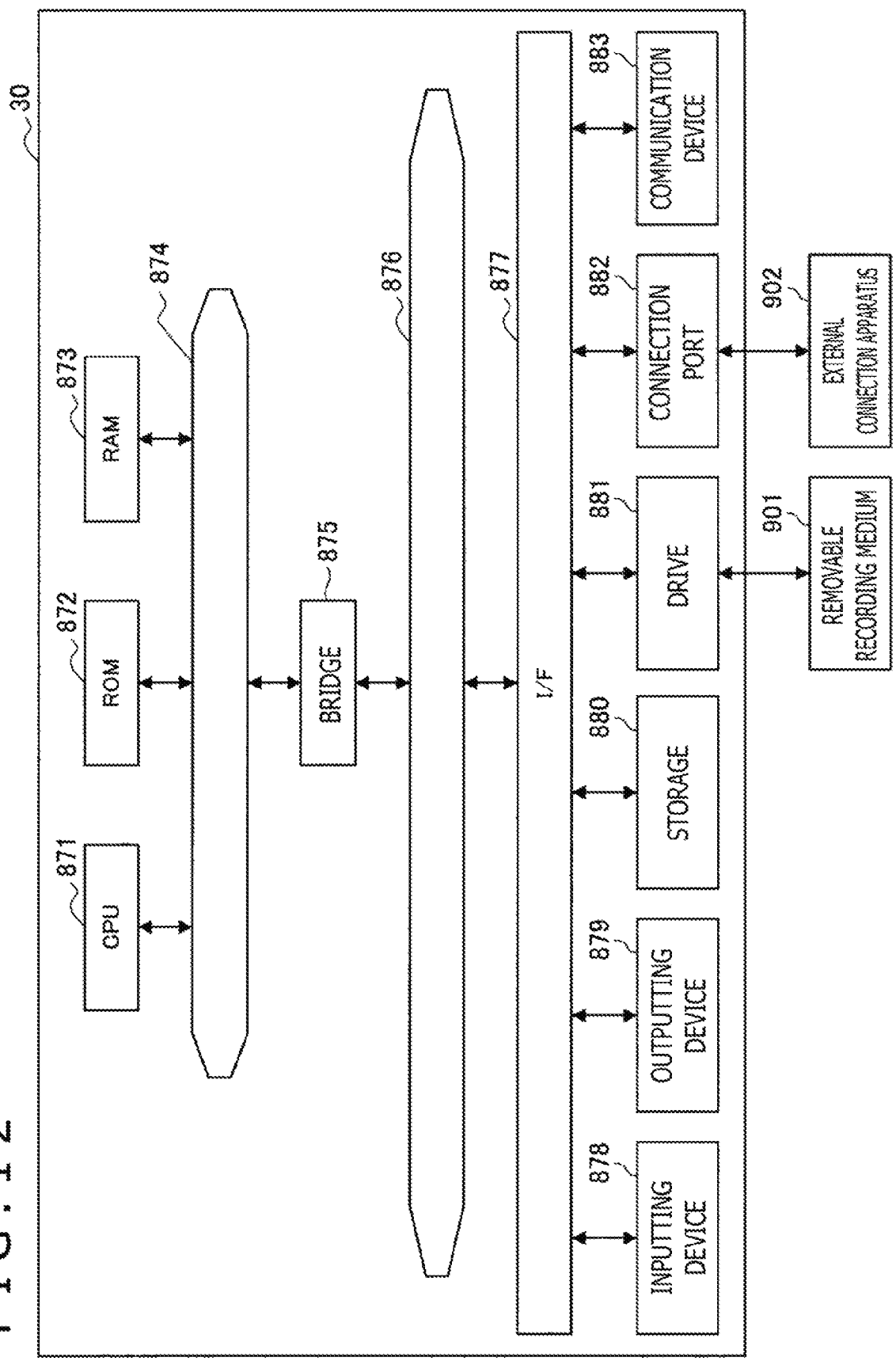
FIG. 12 is a view depicting an example of a hardware configuration of the control device according to the embodiment of the present disclosure.

Now, an example of a hardware configuration of the control device 30 according to the embodiment of the present disclosure is described. FIG. 12 is a block diagram depicting an example of a hardware configuration of the control device 30 according to the embodiment of the present disclosure. Referring to FIG. 12, the control device 30 includes, for example, a CPU 871, a ROM 872, a RAM 873, a host bus 874, a bridge 875, an external bus 876, an interface 877, an inputting device 878, an outputting device 879, a storage 880, a drive 881, a connection port 882, and a communication device 883. It is to be noted that the hardware configuration described here is an example and part of the components may be omitted. Further, components other than the components described here may be additionally included.

(CPU 971)

The CPU 871 functions, for example, as an arithmetic processing device or a control device and controls general operation of the components or part of the operation on the basis of various programs recorded in the ROM 872, RAM 873, storage 880 or a removable recording medium 901.

(ROM 872 and RAM 873)

The ROM 872 is means storing a program to be read into the CPU 871, data to be used for arithmetic operation, and so forth. In the RAM 873, for example, a program to be read into the CPU 871, various parameters that suitably vary when the program is executed, and so forth are stored temporarily or permanently.

(Host Bus 874, Bridge 875, External Bus 876, and Interface 877)

The CPU 871, ROM 872, and RAM 873 are connected to each other, for example, through the host bus 874 capable of implementing high-speed data transmission. Meanwhile, the host bus 874 is connected to the external bus 876 whose data transmission speed is comparatively low, for example, through the bridge 875. Further, the external bus 876 is connected to the various components through the interface 877.

(Inputting Device 878)

For example, a mouse, a keyboard, a touch panel, a button, a switch, a lever, and so forth are used for the inputting device 878. Further, as the inputting device 878, a remote controller (hereinafter referred to as a remote control) capable of transmitting a control signal utilizing an infrared ray or some other electric wave is sometimes used. Further, an audio inputting device such as a microphone is included in the inputting device 878.

(Outputting Device 879)

The outputting device 879 is a device capable of notifying the user of acquired information visually or aurally, such as, for example, a display device like a CRT (Cathode Ray Tube), an LCD or an organic EL, an audio outputting device like a speaker or a headphone, a printer, a mobile phone, or a facsimile.

(Storage 880)

The storage 880 is a device for storing various data therein. As the storage 880, for example, a magnetic storage device such as a hard disk drive (HDD), a semiconductor storage device, an optical storage device, a magneto-optical storage device or the like is used.

(Drive 881)

The drive 881 is a device that reads out information recorded in the removable recording medium 901 such as, for example, a magnetic disk, an optical disk, a magneto-optical disk, or a semiconductor memory or writes information into the removable recording medium 901.

(Removable Recording Medium 901)

The removable recording medium 901 includes, for example, DVD media, Blu-Ray (registered trademark) media, HD DVD media, various semiconductor storage media, or the like. As a matter of course, the removable recording medium 901 may include, for example, an IC card, electronic equipment, or the like in which a non-contacting type IC chip is incorporated.

(Connection Port 882)

The connection port 882 is a port for connecting an external connection apparatus 902 such as, for example, a USB (Universal Serial Bus) port, an IEEE1394 port, an SCSI (Small Computer System Interface), an RS-232C port, an optical audio terminal, or the like.

(External Connection Apparatus 902)

The external connection apparatus 902 includes, for example, a printer, a portable music player, a digital camera, a digital video camera, an IC recorder, or the like.

(Communication Device 883)

The communication device 883 is a communication device for connection to a network and includes, for example, a communication card for a wired or wireless LAN, Bluetooth (registered trademark), or a WUSB (Wireless USB), a router for optical communication, a router for an ADSL (Asymmetric Digital Subscriber Line), a modem for various kinds of communication, or the like.

5. Summary

As described above, the control device 30 according to the embodiment of the present disclosure has the function of correcting a luminance detection value relating to a biological image in accordance with a characteristic of an identified surgical optical device. More in detail, the control device 30 according to the embodiment of the present disclosure has the function of correcting a luminance detection value so as to correct luminance unevenness arising from a biological image in accordance with an identified surgical optical device. With the configuration, exposure control with high accuracy that does not rely upon a characteristic of an optical system can be implemented.

While the suitable embodiment of the present disclosure is described in detail while referring to the drawings, the technical scope of the present disclosure is not limited to this. It is clear that a person having ordinary knowledge in the technical field of the present disclosure is capable of conceiving various alterations or modifications without departing from the technical idea described in claims, and it is recognized that the various examples just described naturally belong to the technical scope of the present disclosure.

Further, the processing steps of the control device 30 according to the embodiment of the present disclosure are not necessarily processed in time series along the order described in the flow chart. For example, the steps according to the processing of the control device 30 may be processed in an order different from that described in the flow chart or may be processed in parallel.

Further, the advantageous effects described in the present specification are merely explanatory or exemplary and are not restrictive. In short, the technology according to the present disclosure can achieve other advantageous effects that are apparent to those skilled in the art from the description of the present specification together with or in place of the advantageous effects described above.

It is to be noted that also such configurations as described below belong to the technical scope of the present technology.

(1)
A surgical controlling device including:
an exposure controlling section configured to perform exposure control based on a luminance detection value detected from a biological image, in which
the exposure controlling section corrects, on the basis of information regarding an identified surgical optical device, the luminance detection value so as to correct luminance unevenness arising from the surgical optical device.

(2)
The surgical controlling device according to (1) above, in which
the exposure controlling section specifies a luminance correction value on the basis of information regarding the identified surgical optical device and corrects the luminance detection value using the luminance correction value.

(3)
The surgical controlling device according to (1) or (2) above, in which
the luminance unevenness includes at least one of shading arising from the surgical optical device or a black area, and
the exposure controlling section corrects the luminance detection value so as to correct a luminance variation arising from at least one of the shading or the black area.

(4)
The surgical controlling device according to any one of (1) to (3) above, in which
the exposure controlling section detects an imaging object having a luminance equal to or higher than a given threshold value in the biological image and corrects the luminance detection value using a luminance correction value corresponding to a position of the imaging object in the biological image.

(5)
The surgical controlling device according to (4) above, in which
the exposure controlling section calculates a distance from the center of the biological image to the imaging object and corrects the luminance detection value using the luminance correction value corresponding to the distance.

(6)
The surgical controlling device according to any one of (1) to (5) above, in which
the surgical optical device includes at least one of a surgical imaging device or an irradiation device, and
the exposure controlling section corrects the luminance detection value so as to correct the luminance unevenness arising from at least one of the surgical imaging device or the irradiation device.

(7)
The control device according to (6) above, in which
the surgical imaging device is configured from an endoscope.

(8)
The surgical controlling device according to any one of (1) to (7) above, in which
the exposure controlling section corrects the luminance detection value using a plurality of luminance correction values individually corresponding to a plurality of the surgical optical devices.

(9)
The surgical controlling device according to any one of (1) to (8) above, in which
the exposure controlling section corrects the luminance detection value using values obtained by multiplication of a plurality of luminance correction values individually corresponding to a plurality of the surgical optical devices.

(10)
The surgical controlling device according to any one of (1) to (9) above, in which
the information regarding the surgical optical device is identified on the basis of received identification information.

(11)
The surgical controlling device according to any one of (1) to (9) above, in which
the information regarding the surgical optical device is identified on the basis of the biological image.

(12)
The surgical controlling device according to any one of (1) to (11) above, in which
the exposure controlling section corrects the luminance detection value in accordance with a direction of the identified surgical optical device.

(13)
The surgical controlling device according to any one of (1) to (12) above, further including:
an identification section configured to identify the surgical optical device.

(14)
The surgical controlling device according to any one of (1) to (13) above, in which
the exposure controlling section generates a luminance value histogram on the basis of the luminance detection value, calculates a first peak median and a second peak median in the luminance value histogram and performs exposure control on the basis of a degree of separation of the first peak median and the second peak median.

(15)
The surgical controlling device according to (14) above, in which
the exposure controlling section executes the exposure control in a case where the degree of separation is equal to or higher than a threshold value.

(16)
A control method including:
performing, by a processor, exposure control based on a luminance detection value detected from a biological image, in which
the performing the exposure control further includes correcting the luminance detection value so as to correct, on the basis of information regarding an identified surgical optical device, luminance unevenness arising from the surgical optical device.

(17)
A surgical system including:
a surgical optical device used to capture a biological image; and
a surgical controlling device configured to perform exposure control based on a luminance detection value detected from the biological image, in which
the surgical controlling device corrects, on the basis of information regarding the identified surgical optical device, the luminance detection value so as to correct luminance unevenness arising from the surgical optical device.

(18)
A program for causing a computer to function as
a surgical controlling device including an exposure controlling section that performs exposure control based on a luminance detection value detected from a biological image, in which
the exposure controlling section corrects, on the basis of information regarding an identified surgical optical device, the luminance detection value so as to correct luminance unevenness arising from the surgical optical device.

REFERENCE SIGNS LIST

10 Imaging device
110 Imaging section
120 Communication section
20 Irradiation device
210 Irradiation section
220 Communication section
30 Control device
310 Exposure controlling section
320 Identification section
330 Image processing section
340 Communication section

The invention claimed is:

1. A surgical controlling device comprising:
one or more processors configured to:
perform exposure control based on a luminance detection value detected from a biological image;
detect, in the biological image, an imaging object having a luminance higher than a given threshold value;
calculate a distance from a center of the biological image to a position, in the biological image, of the imaging object having the luminance higher than the given threshold value; and
correct, based on information regarding an identified surgical optical device, the luminance detection value so as to correct luminance unevenness, in the biological image, arising from the identified surgical optical device, wherein the luminance detection value is corrected using a luminance correction value that corresponds to the calculated distance.

2. The surgical controlling device according to claim 1, wherein
the one or more processors are configured to specify the luminance correction value based on the information regarding the identified surgical optical device.

3. The surgical controlling device according to claim 1, wherein
the luminance unevenness includes at least one of shading arising from the identified surgical optical device or a black area in the biological image, and
the luminance detection value is corrected so as to correct a luminance variation arising from at least one of the shading or the black area.

4. The surgical controlling device according to claim 1, wherein
the luminance correction value further corresponds to the position, in the biological image, of the imaging object.

5. The surgical controlling device according to claim 1, wherein
the identified surgical optical device includes at least one of a surgical imaging device or an irradiation device, and
the luminance detection value is corrected so as to correct the luminance unevenness arising from at least one of the surgical imaging device or the irradiation device.

6. The surgical controlling device according to claim 5, wherein the surgical imaging device is configured from an endoscope.

7. The surgical controlling device according to claim 1, wherein
the luminance detection value is corrected using a plurality of luminance correction values individually corresponding to a plurality of surgical optical devices, wherein the plurality of surgical optical devices includes the identified surgical optical device, and wherein the plurality of luminance correction values includes the luminance correction value.

8. The surgical controlling device according to claim 1, wherein
the luminance detection value is corrected using values obtained by multiplication of a plurality of luminance correction values individually corresponding to a plurality of surgical optical devices, wherein the plurality of surgical optical devices includes the identified surgical optical device, and wherein the plurality of luminance correction values includes the luminance correction value.

9. The surgical controlling device according to claim 1, wherein
the one or more processors are further configured to identify the information regarding the surgical optical device based on received identification information.

10. The surgical controlling device according to claim 1, wherein
the one or more processors are further configured to identify the information regarding the surgical optical device based on the biological image, and wherein the identified information regarding the surgical optical device includes a model of the surgical optical device.

11. The surgical controlling device according to claim 1, wherein
the one or more processors are further configured to identify, based on the biological image, a direction of the surgical optical device, and wherein the luminance detection value is corrected in accordance with the identified direction of the identified surgical optical device.

12. The surgical controlling device according to claim 11, wherein
the one or more processors are further configured to identify the direction of the surgical optical device based on a shape of a light source emission port that is included in the surgical optical device and pictured in the biological image.

13. The surgical controlling device according to claim 11, wherein
the one or more processors are further configured to identify the direction of the surgical optical device further based on sensor information from a geomagnetic sensor or a gyroscopic sensor in the surgical optical device.

14. The surgical controlling device according to claim 1, wherein
the one or more processors are further configured to identify the surgical optical device.

15. The surgical controlling device according to claim 1, wherein the one or more processors are further configured to:
generate a luminance value histogram based on the luminance detection value; and
calculate a first peak median and a second peak median in the luminance value histogram, wherein the exposure control is performed further based on a degree of separation of the first peak median and the second peak median.

16. The surgical controlling device according to claim 15, wherein
the exposure control is performed in a case where the degree of separation is equal to or higher than a threshold value.

17. The surgical controlling device according to claim 1, wherein the one or more processors are further configured to receive identification information including a model of the surgical optical device, and wherein the information regarding the surgical optical device is identified based on the received identification information.

18. A control method comprising:
performing, by a processor, exposure control based on a luminance detection value detected from a biological image, wherein
the performing of the exposure control further includes:
  detecting, by the processor, in the biological image, an imaging object having a luminance higher than a given threshold value;
  calculating, by the processor, a distance from a center of the biological image to a position, in the biological image, of the imaging object having the luminance higher than the given threshold value; and
  correcting, by the processor, the luminance detection value to correct, based on information regarding an identified surgical optical device, luminance unevenness, in the biological image, arising from the identified surgical optical device, wherein the luminance detection value is corrected using a luminance correction value that corresponds to the calculated distance.

19. A surgical system comprising:
a surgical optical device used to capture a biological image; and
a surgical controlling device including one or more processors configured to:
  perform exposure control based on a luminance detection value detected from the biological image;
  detect, in the biological image, an imaging object having a luminance higher than a given threshold value;
  calculate a distance from a center of the biological image to a position, in the biological image, of the imaging object having the luminance higher than the given threshold value; and
  correct, based on information regarding the surgical optical device, the luminance detection value so as to correct luminance unevenness, in the biological image, arising from the surgical optical device, wherein the luminance detection value is corrected using a luminance correction value that corresponds to the calculated distance.

20. A non-transitory computer-readable medium having stored thereon, computer-executable instructions which, when executed by a processor, cause the processor to execute operations, the operations comprising:
performing exposure control based on a luminance detection value detected from a biological image;
detecting, in the biological image, an imaging object having a luminance higher than a given threshold value;
calculating a distance from a center of the biological image to a position, in the biological image, of the imaging object having the luminance higher than the given threshold value; and
correcting based on information regarding an identified surgical optical device, the luminance detection value so as to correct luminance unevenness, in the biological image, arising from the identified surgical optical device, wherein the luminance detection value is corrected using a luminance correction value that corresponds to the calculated distance.

* * * * *